United States Patent
Szewczyk et al.

(10) Patent No.: US 9,744,112 B2
(45) Date of Patent: *Aug. 29, 2017

(54) FILM CONTAINING COMPOSITIONS

(75) Inventors: Gregory Szewczyk, Flemington, NJ (US); Neeta Atul Patel, Monmouth Junction, NJ (US); Suzanne Jogun, Wayne, NJ (US); Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/365,116

(22) PCT Filed: Dec. 16, 2011

(86) PCT No.: PCT/US2011/065308
§ 371 (c)(1),
(2), (4) Date: Jun. 13, 2014

(87) PCT Pub. No.: WO2013/089759
PCT Pub. Date: Jun. 20, 2013

(65) Prior Publication Data
US 2014/0322141 A1 Oct. 30, 2014

(51) Int. Cl.
*A61Q 11/00* (2006.01)
*A61K 8/00* (2006.01)
*A61K 8/34* (2006.01)
*A61K 8/49* (2006.01)
*A61K 8/58* (2006.01)
*A61K 8/73* (2006.01)
*A61K 8/02* (2006.01)

(52) U.S. Cl.
CPC .................. *A61K 8/58* (2013.01); *A61K 8/02* (2013.01); *A61K 8/0216* (2013.01); *A61K 8/494* (2013.01); *A61K 8/731* (2013.01); *A61Q 11/00* (2013.01); *A61K 2800/43* (2013.01); *A61K 2800/58* (2013.01)

(58) Field of Classification Search
USPC ......................................................... 424/49
See application file for complete search history.

(56) References Cited

U.S. PATENT DOCUMENTS

| | | | |
|---|---|---|---|
| 3,662,059 A | 5/1972 | Wiesner | |
| 6,136,297 A | 10/2000 | Sagel et al. | |
| 6,419,902 B1 | 7/2002 | Wright | |
| 6,419,903 B1 | 7/2002 | Xu et al. | |
| 6,479,036 B1 | 11/2002 | Stanier et al. | |
| 6,669,229 B2 | 12/2003 | Thomas | |
| 7,763,235 B2 | 7/2010 | Boyd et al. | |
| 2002/0034479 A1 | 3/2002 | Green | |
| 2004/0136924 A1* | 7/2004 | Boyd | A61K 8/042 424/48 |
| 2004/0247646 A1 | 12/2004 | Ivory et al. | |
| 2005/0019273 A1 | 1/2005 | Boyd et al. | |
| 2006/0035008 A1 | 2/2006 | Virgallito et al. | |
| 2006/0134020 A1 | 6/2006 | Robinson et al. | |
| 2007/0020201 A1 | 1/2007 | Boyd et al. | |
| 2007/0148213 A1 | 6/2007 | Ibrahim et al. | |
| 2008/0138369 A1 | 6/2008 | Boyd et al. | |
| 2008/0160056 A1 | 7/2008 | Boyd et al. | |
| 2008/0187497 A1 | 8/2008 | Agarwal et al. | |
| 2008/0187498 A1 | 8/2008 | Francis | |
| 2008/0245678 A1 | 10/2008 | Gantenberg | |
| 2008/0247967 A1 | 10/2008 | Sagel | |
| 2008/0247968 A1 | 10/2008 | Sagel | |
| 2008/0247969 A1 | 10/2008 | Glandorf | |
| 2008/0247970 A1 | 10/2008 | Gantenberg | |
| 2008/0248072 A1 | 10/2008 | Glandorf | |
| 2008/0248073 A1 | 10/2008 | Gantenberg | |
| 2008/0260836 A1 | 10/2008 | Boyd | |
| 2009/0060597 A1 | 3/2009 | Yoshida et al. | |

FOREIGN PATENT DOCUMENTS

| | | |
|---|---|---|
| EP | 0255210 | 2/1988 |
| EP | 1843738 | 10/2007 |
| EP | 2105122 | 9/2009 |
| EP | 2116216 | 11/2009 |
| TW | 201102095 | 1/2011 |
| TW | 201129392 | 9/2011 |
| WO | WO 2008/008617 | 1/2008 |
| WO | WO2010114551 | 10/2010 |
| WO | WO2012082098 | 6/2012 |
| WO | WO2012082103 | 6/2012 |
| WO | WO2012087328 | 6/2012 |

OTHER PUBLICATIONS

"Dissolution (Chemistry)," Wikipedia, Aug. 14, 2012, XP002683426, Retrieved from the internet: URL:http//en.wikipedia.org/wiki/Dissolution_(chemistry).
International Search Report and the Written Opinion issued in International Application PCT/US2011/65308 mailed Oct. 25, 2012. WO.
Written Opinion of the International Preliminary Examining Authority issued in International Application PCT/US2011/65308 mailed Jan. 29, 2014. WO.

* cited by examiner

*Primary Examiner* — Lezah Roberts

(57) ABSTRACT

Described herein are compositions comprising a film, wherein the film comprises a pigment, and is adapted to release the pigment at a specific point in time during use; and methods of making and using the same.

7 Claims, No Drawings

FILM CONTAINING COMPOSITIONS

CROSS-REFERENCE TO RELATED PATENT APPLICATIONS

The present application is a U.S. national stage entry under 35 U.S.C.§371 of Patent Cooperation Treaty Patent Application No. PCT/US2011/65308, filed Dec. 16, 2011, the entirety of which is incorporated herein by reference.

BACKGROUND

It is recommended that children should brush their teeth for at least 45-60 seconds, and adults for at least 90 to 120 seconds. Most people, especially children, do not brush their teeth for a sufficient period of time to obtain maximum benefit, and moreover have difficulty accurately estimating the time necessary to brush the teeth.

There is a need for toothpastes comprising films, which deliver a color change signal after brushing for appropriate period of time, and optionally deliver an active ingredient during the brushing period; thereby encouraging users to brush their teeth for a longer period of time.

SUMMARY

In some embodiments, the present invention provides oral care compositions comprising films comprising a pigment, wherein release of the pigment upon use is controlled by the thickness of the films, for example oral care compositions comprising color-changing films, which are attractive and stable in the formulation and provide a color change signal after a sufficient period of use. In some embodiments, the compositions comprise a second film.

The present inventors have developed compositions comprising films or capsules comprising a high concentration of pigment, which would be stable in formulation, but are adapted to provide a color change after a sufficient period of brushing. The user would be instructed to continue brushing until the color change was observed, to help ensure that they have brushed for a sufficient period of time. One difficulty presented in formulating such a product is to reliably control the length of time required to brush using the toothpaste before the color changed. The present inventors also encountered and overcame difficulties in assuring that the pigment would be substantially released at a specific point in time, and that it would not slowly leak from the film.

Several approaches to control the time it took for the toothpaste to deliver a color during brushing were tried. The data described herein demonstrates that the timing of the color change can be adjusted through the film composition, and in particular the thickness of the film, to occur at a specified time so as to provide a visual signal to a consumer at the appropriate time, i.e., when enough time has been spent brushing. The data generated demonstrates that a more hydrophobic, less soluble, or higher molecular weight polymer system slows disintegration into water. Surprisingly, however, when comparing the same film formulation and only changing thickness (1, ~1.5, ~2.5, ~3.0 mil) the first evidence of color release is altered. This trend continues for the first visual determination of color when the two different thickness films are evaluated during actual brushing.

With films that have pigment uniformly dispersed throughout, it might be predicted that the rate of release would be independent of the thickness. This is not the case, however. Even though the same weight amount of strips are present, the thicker film takes more than twice as long to be first noticed for color release. By controlling film thickness in the product, we found that it is possible to control release of an active in the film. The rate of dissolution is inversely proportional to the thickness; as the thickness of the films increase the rate of dissolution disproportionately decreases. For example, a doubling in film thickness results in a decrease in dissolution greater than 2×. By making all the film the same predetermined thickness, the release of active can be delayed for a predetermined period of brushing or scrubbing followed by release in a burst, as in the case of the color change toothpaste. By using films of varying predetermined thicknesses, release can be spread out over a period of brushing or scrubbing, as first the thinner films than the thicker films release active, or the nature of the release can be changed over time, for example providing a different color, taste or fragrance, as one active is released from the thinner films and another from the thicker films. Generally, the film comprises a more hydrophobic, less soluble, or higher molecular weight polymer system to slow disintegration into the water. The active can be any active, generally one that is substantially water insoluble, for example a pigment, fragrance, flavor, topical anesthetic, or topical antibacterial agent.

Accordingly, some embodiments of the present invention provide a method for controlling the timing of release of an active, for example a pigment, flavor, fragrance, topical antibacterial agent, or topical anesthetic agent from a film fragment in a product which is subjected to agitation and moisture during use, e.g., in a personal care product which is applied by brushing or scrubbing, for example a toothpaste, or in a chewing gum, comprising controlling the thickness of the film fragment to control the timing of the release, including a method for providing release after a predetermined amount of brushing or scrubbing, a method of providing sustained release by providing film fragments of varying thickness, and a method for providing release of different actives at different points in time, comprising providing one active in a thinner film and a different active in a thicker film.

Some embodiments of the present invention further provide a product which is subjected to agitation and moisture during use, e.g., an oral care product which is applied by brushing or scrubbing, for example a toothpaste, comprising varying film fragments of a predetermined thickness comprising an active, e.g., a pigment, including the product wherein the fragments are all of substantially the same thickness such that the active is released after a predetermined amount of brushing or scrubbing, as well as the product comprising film fragments of varying thickness such that the active is released over a sustained period or different actives are released at different predetermined periods. The invention also provides the use of a film of predetermined thickness comprising an active agent to control release of the active, e.g., in accordance with the foregoing methods or in the manufacture of the foregoing products.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

Some embodiments of the present invention provide a dissolvable film (Film 1) of predetermined thickness comprising an active ingredient, wherein the dissolution rate in aqueous media is inversely proportional to the thickness, such that the film will disintegrate and release active ingredient in the presence of water at room temperature (e.g., 20-25° C.) after a period of greater than 30 seconds, for example:

1.1. Film 1 wherein the film comprises cellulose ethers, e.g., selected from
  (i) alkylcellulose, e.g., methylcellulose;
  (ii) hydroxyalkyl cellulose, e.g., selected from hydroxypropyl methyl cellulose, hydroxyethylpropyl cellulose, hydroxybutyl methyl cellulose, hydroxy propyl methyl cellulose, carboxymethyl cellulose and mixtures thereof;
  and (iii) mixtures thereof
1.2. Any of the foregoing films comprising a starch, e.g. a pregelatinized starch;
1.3. Any of the foregoing films comprising a plasticizer, e.g., a polyalcohol, e.g., sorbitol, propylene glycol, glycerol, or low molecular weight polyethylene glycol, e.g., PEG 200;
1.4. Any of the foregoing films comprising propylene glycol, e.g., in an amount effective to provide plasticity to the film, e.g., about 20-30% by dry weight of the film;
1.5. Any of the foregoing films comprising a non-ionic surfactant or emulsifier, e.g., a polysorbate, e.g., polysorbate 80 (also known as polyoxyethylene(20) sorbitan monooleate, available commercially e.g., as Tween® 80), e.g., in an amount of about 1-5% by dry weight of the film;
1.1. Any of the foregoing films comprising a pigment, e.g., a red pigment, for example D&C Red 30, a green pigment, for example Pigment Green 7, a blue pigment, for example a phthalocyanine, for example Pigment Blue 15:

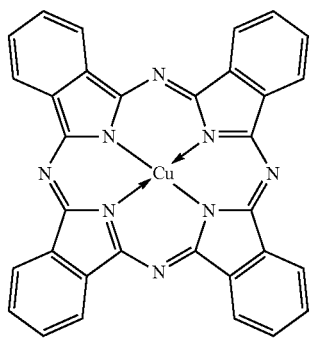

or a combination of any of these pigments.
1.6. Any of the foregoing films comprising which is substantially dissolved after a period of greater than 30 seconds and less than 180 seconds of brushing, scrubbing or agitation in the oral cavity or on the skin in the presence of water;
1.7. Any of the foregoing films wherein the average thickness of the film is 1-4 mil, e.g. 1.5-3 mil, e.g. about 1.5 mil or about 3 mil;
1.8. Any of the foregoing films comprising, by dry weight of the film, 20-60% cellulose ethers selected from methyl cellulose, hydroxypropylmethyl cellulose, and mixtures thereof; 10-30% propylene glycol; 1-5% polysorbate 80; and 15-55% pigment;
1.9. Any of the foregoing films wherein the active is selected from pigments, flavors, fragrances, antibacterial agents, anesthetic agents or combinations thereof;
1.10. Any of the foregoing films in the form of film fragments, e.g., regular or irregular shapes or flakes;
1.11. Any of the foregoing films in the form of film fragments, e.g., regular or irregular shapes or flakes comprising a first population of film fragments of predetermined thickness, a second population of film fragments of predetermined thickness wherein the thickness of the second population is 1.5-3 times the thickness of the first population, and optionally a third population wherein the thickness of the third population is 1.5-3 times the thickness of the second population;
1.12. Any of the foregoing films which are topically acceptable;
1.13. Any of the foregoing films which are orally acceptable;
1.14. Any of the foregoing films comprising an antibacterial agent selected from triclosan and essential oils from plant extracts, e.g., menthol.

The invention also provides a product (Product 1) which is subjected to agitation and moisture during use, comprising film fragments of a predetermined thickness comprising an active such that the active is released during use after a predetermined time of agitation, e.g. after brushing, scrubbing or chewing for a predetermined time, e.g. a product comprising fragments of any of Film 1, et seq.

1.1. Product 1 wherein the product is a an oral care product, an oral care product, e.g., a dentifrice, for example a toothpaste, e.g., a clear gel or opaque toothpaste, comprising orally acceptable dissolvable film fragments, e.g., fragments of any of Film 1;
1.2. Product 1 or 1.1 wherein the product is a clear gel or opaque toothpaste and the film fragment comprises a pigment that is released upon dissolution of the film thereby changing the color of the toothpaste after brushing for a period of 30-180 seconds, e.g., about 45-60 seconds in a toothpaste for use by a child or about 90-120 seconds in a toothpaste for use by an adult, thereby releasing the pigment and providing a color signal to the user of adequate brushing;
1.3. Product 1 wherein the product is a hand or body soap;
1.4. Product 1 wherein the product is a chewing gum and the active is a flavoring or topical anesthetic or topical antibacterial agent;
1.5. Any of the foregoing products wherein the fragments are all of substantially the same thickness such that the active is released after a predetermined amount of agitation, brushing or scrubbing;
1.6. Any of the foregoing products 1-1.4 comprising a first population of film fragments of predetermined thickness, a second population of film fragments of predetermined thickness wherein the thickness of the second population is 1.5-3 times the thickness of the first population, and optionally a third population wherein the thickness of the third population is 1.5-3 times the thickness of the second population;
1.7. Product 1.6, wherein the active is released in a controlled way after a predetermined amount of agitation, brushing or scrubbing with the first population releasing first and the second population releasing second and the third population when present releasing third;

1.8. Product 1.7 wherein the populations of film fragments comprise the same active such that the active is released over a sustained period as the different populations release sequentially;

1.9. Product 1.7 wherein the different populations each comprise different actives which are released sequentially;

1.10. Product 1.9 which is a chewing gum wherein the different actives are different flavorings, such that the chewing gum changes flavor over time.

The invention provides, in another embodiment, a method for controlling timing of release of an active from a film fragment in a product which is subjected to agitation and moisture during use, comprising controlling the thickness of the film fragment to control the timing of the release during use after a predetermined time of agitation (Method 1); for example, 1.2. Method 1 wherein the film fragments comprising active are all substantially the same thickness such that release occurs in a controlled release after a predetermined period of agitation;

1.3. Method 1 wherein the film fragments are of different predetermined thicknesses, such that sustained release occurs as the film fragments of different predetermined thicknesses release active at different predetermined times during use;

1.4. Method 1 or 1.2 wherein a first active is provided in a thinner film fragment and a second active in a thicker film fragment, such that release of the first active occurs first and the second active occurs second, for example to provide a color change to a first color upon release of a first pigment and a second color on release of a second pigment, or a flavor or fragrance change upon release of a first then a second flavor or fragrance;

1.5. Any of the foregoing methods wherein the active is substantially water insoluble, e.g. has a solubility in water at room temperature of less than 1%;

1.6. Any of the foregoing methods wherein the active is a pigment;

1.7. Any of the foregoing methods wherein the active is a fragrance;

1.8. Any of the foregoing methods wherein the active is a flavor;

1.9. Any of the foregoing methods wherein the active is an antibacterial agent;

1.10. Any of the foregoing methods wherein the active is an anesthetic agent;

1.11. Any of the foregoing methods wherein the product is a toothpaste;

1.12. Any of the foregoing methods wherein the product is a hand or body soap;

1.13. Any of the foregoing methods wherein the product is a chewing gum;

1.14. Any of the foregoing methods wherein the product is a toothpaste and the film fragment comprises a pigment that is released upon dissolution of the film;

1.15. Any of the foregoing methods wherein the film fragment will not disintegrate in water at room temperature in less than 5 minutes in the absence of agitation;

1.16. Any of the foregoing methods wherein the film fragments comprise cellulose ethers, e.g., selected from
(i) alkylcellulose, e.g., methylcellulose;
(ii) hydroxyalkyl cellulose, e.g., selected from hydroxypropyl methyl cellulose, hydroxyethylpropyl cellulose, hydroxybutyl methyl cellulose, hydroxy propyl methyl cellulose, carboxymethyl cellulose and mixtures thereof;
and (iii) mixtures thereof;

1.17. Any of the foregoing methods wherein the film fragments comprise a starch, e.g. a pregelatinized starch;

1.18. Any of the foregoing methods wherein the film fragments comprise a plasticizer, e.g., a polyalcohol, e.g., sorbitol, propylene glycol, glycerol, or low molecular weight polyethylene glycol, e.g., PEG 200;

1.19. Any of the foregoing methods wherein the film fragments comprise propylene glycol, e.g., in an amount effective to provide plasticity to the film, e.g., about 20-30% by dry weight of the film;

1.20. Any of the foregoing methods wherein the film fragments comprise a non-ionic surfactant or emulsifier, e.g., a polysorbate, e.g., polysorbate 80 (also known as polyoxyethylene(20) sorbitan monooleate, available commercially e.g., as Tween® 80), e.g., in an amount of about 1-5% by dry weight of the film;

1.21. Any of the foregoing methods wherein the film fragments comprise a pigment, e.g., a red pigment, for example D&C Red 30, a green pigment, for example Pigment Green 7, a blue pigment, for example a phthalocyanine, for example Pigment Blue 15:

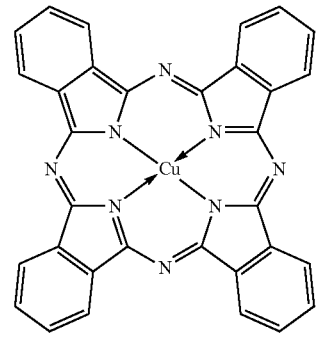

or a combination of any of these pigments.

1.22. Any of the foregoing methods wherein the film fragments are substantially dissolved after a period of greater than 30 seconds and less than 180 seconds of brushing, scrubbing or agitation in the presence of water;

1.23. Any of the foregoing methods wherein the average thickness of the film fragments is 0.5-2 mil, e.g., about 1 mil;

1.24. Any of the foregoing methods wherein the film fragments comprise, by dry weight of the film fragments, 20-60% cellulose ethers selected from methyl cellulose, hydroxypropylmethyl cellulose, and mixtures thereof; 10-30% propylene glycol; 1-5% polysorbate 80; and 15-55% pigment.

1.25. Any of the foregoing methods wherein the fragments are any of Film 1, et seq., or wherein the product is any of Product 1, et seq.

The invention further provides a method of cleaning the teeth comprising brushing with a toothpaste comprising an orally acceptable dissolvable film of predetermined thickness, e.g., Product 1.1 or 1.2, wherein brushing is continued until the film disintegrates and the pigment provides a color signal to the user of adequate brushing, for example, wherein the brushing time before the film matrix dissolves is between 30 and 180 seconds, e.g., about 45-60 seconds for a toothpaste for use by a child and about 90-120 seconds for a toothpaste for use by an adult.

In some embodiments, the composition is a clear gel toothpaste; wherein the pigment is released from the first film after brushing for a period of 30 to 120 seconds. In some embodiments, the pigment is released from the first film after brushing for a period of 60 seconds. In some embodiments, the pigment is released from the first film after brushing for a period of 90 seconds. In some embodiments, the pigment is released from the first film after brushing for a period of 120 seconds.

The invention further provides a method of cleaning the teeth, removing plaque, treating halitosis, or treating gingivitis comprising brushing the teeth with 1.1 or 1.2.

The invention further provides the use of a dissolvable film of predetermined thickness comprising an active agent to control release of the active, e.g., in accordance with the foregoing methods or in the manufacture of the foregoing products.

In some embodiments, the present invention provides an oral care composition comprising a first film comprising a pigment, wherein the first film has a dissolution rate in aqueous media that is inversely proportional to its thickness, such that the film will disintegrate and release the pigment in the presence of water at room temperature after a period of greater than 30 seconds.

In some embodiments, the film comprises a cellulose ether selected from: an alkylcellulose; a hydroxylalkyl cellulose; and a combination thereof. In some embodiments, the alkylcellulose is methylcellulose. In some embodiments, the hydroxyalkyl cellulose is selected from: hydroxypropyl methyl cellulose, hydroxyethylpropyl cellulose, hydroxybutyl methyl cellulose, hydroxy propyl methyl cellulose, carboxymethyl cellulose and a combination of two or more thereof Some embodiments of the present invention further comprise a plasticizer selected from sorbitol, propylene glycol, glycerol, and low molecular weight polyethylene glycol. Further embodiments comprise a polysorbate.

In some embodiments, the film is substantially dissolved after a period of greater than 30 seconds and less than 180 seconds of brushing, scrubbing or agitation in the presence of water.

Some embodiments provide a composition, further comprising a second film having a dissolution rate in aqueous media that is faster than the dissolution rate in aqueous media of said first film, wherein said second film comprises an active agent selected from an antibacterial agent; a flavor, a fragrance; and a combination of two or more thereof.

In some embodiments, the first and/or second film are provided in the form of film fragments having regular or irregular shapes.

In some embodiments, substantially all of the pigment is released from the first film at the same point in time.

Other embodiments provide a method for controlling release of a pigment from a film in a composition which is subjected to agitation and moisture during use, comprising controlling the thickness of the film fragment to control the timing of the release during use after a predetermined amount of agitation.

Yet other embodiments provide a method of cleaning the teeth comprising brushing with a toothpaste according to any foregoing claim, wherein brushing is continued until the film releases substantially all of the pigment; thereby providing a color signal to the user of adequate brushing.

In some embodiments, substantially all of the pigment is released at one time. As used herein, the term "substantially all" refers to greater than 90% of the total amount of pigment contained in the film. In some embodiments, the first film releases at least 90% of the total amount of pigment contained therein, at a particular point in time. In some embodiments, the first film releases greater than 90% of the total amount of pigment contained therein, at a designated point in time. In some embodiments, the first film releases at least 91% of the total amount of pigment contained therein, at the designated point in time. In some embodiments, the first film releases at least 95% of the total amount of pigment contained therein, at the designated point in time. In some embodiments, the first film releases at least 96% of the total amount of pigment contained therein, at the designated point in time. In some embodiments, the first film releases at least 97% of the total amount of pigment contained therein, at the designated point in time. In some embodiments, the first film releases at least 98% of the total amount of pigment contained therein, at the designated point in time. In some embodiments, the first film releases at least 99% of the total amount of pigment contained therein, at the designated point in time.

Orally acceptable or topically acceptable: The compositions of the invention are intended for topical use in the mouth or on the skin, thus components for use in the present invention should be orally acceptable, that is, safe for topical use in the mouth, in the amounts and concentrations provided.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight.

EXAMPLE

Example 1

A prototype film is developed by encapsulating a pigment into a dissolvable polymer film. During brushing, the films swell from water and disintegrate, releasing the pigment and, thus, color change occurs to indicate the consumer when the brushing is done. One use for this film is for incorporation into a clear gel or opaque toothpaste providing a color change signal to the consumer after a predetermined brushing time, e.g., 45-60 sec for children and 90-120 sec for the adults.

The ingredients for the prototype film are set forth in Table 1:

TABLE 1

|  | Weight % of solids |
|---|---|
| Hydroxypropyl methyl cellulose (Methocel E5) | 7 |
| Methyl cellulose (Methocel A15) | 46.5 |
| Pigment (Vibracolor Blue PBL15) | 19.5 |

TABLE 1-continued

|  | Weight % of solids |
|---|---|
| Propylene Glycol | 25 |
| Tween 80 | 2 |
| Total Amount | 100 |

The prototype film is made in different thicknesses, and flakes of the prototype film are incorporated into a clear gel toothpaste for testing. A dissolution test in vitro is performed by permitting a 1"×1" swatch of bulk film to float on a container filled with 1 L of tap water at room temperature. The effect on film dissolution caused by changes in thickness can be observed and measured over a period of time. As seen on Table 2, the time before pigment release is seen to be approximately proportional to the thickness of the film:

TABLE 2

Dissolution Test
Blue Pigment—A15

| Avg. Film Thickness (mil) | Weight (g) | Density (g/in3) | First hint of color (sec) | First tear of film (sec) | Dissolution time (sec) |
|---|---|---|---|---|---|
| 1.017 | 0.0156 | 15.3442 | 45 | 50 | 110 |
| 1.683 | 0.0306 | 18.1786 | 95 | 155 | 360 |
| 2.683 | 0.0466 | 17.3686 | 137 | 450 | 1055 |
| 3.000 | 0.0621 | 20.7000 | 126 | 805 | 1295 |

Toothpaste comprising flakes of 1.5 mil in thickness and toothpaste comprising flakes of 3 mil in thickness are then tested side by side in a clinical trial. Dissolution occurs more quickly with actual brushing in the mouth compared to the in vitro test, which does not involve brushing, but the correlation between thickness and release time is maintained:

TABLE 3

| Trial | Dissolution time 1.5 mil first color (seconds) | Dissolution time 3.0 mil first color (seconds) | Dissolution time 1.5 mil max color (seconds) | Dissolution time 3.0 mil max color (seconds) |
|---|---|---|---|---|
| 1 | 26 | 45 | 57 | 105 |
| 2 | 30 | 60 | 25 | 45 |
| 3 | 30 | 35 | 35 | 45 |
| 4 | 60 | 120 | 120 | 180 |
| 5 | 76 | 133 | 126 | 120 |
| 6 | 18 | 71 | 37 | 110 |
| 7 | 10 | 30 | 25 | 60 |
| 8 | 20 | 40 | 28 | 50 |
| 9 | 35 | 60 | 45 | 90 |
| Avg | 33.89 | 66.00 | 55.33 | 89.44 |

The release profile of the 1.5 mil film is within the target for use in a children's toothpaste, whereas the release profile for the 3 mil matches the target for use in an adult toothpaste.

The invention claimed is:

1. An oral care composition comprising a first film comprising a pigment; and optionally a second film;
   wherein the first film has a dissolution rate in aqueous media that is inversely proportional to its thickness, such that the first film will disintegrate and release the pigment in the presence of water at room temperature after a period of greater than 30 seconds; and wherein the first film is substantially dissolved after a period of greater than 30 seconds and less than 180 seconds of brushing, scrubbing or agitation in the presence of water;
   wherein the average thickness of the first film is 1.5 - 3 mil; and
   wherein the composition comprises, by dry weight of the first film, 20-60% of a cellulose ether selected from methyl cellulose, hydroxypropyl methyl cellulose, and a combination thereof; 10-30% propylene glycol; 1-5% polysorbate 80; and 15-55% pigment.

2. The composition according to claim 1, wherein the cellulose ether is methylcellulose.

3. The composition according to claim 1, wherein the first film further comprises a plasticizer selected from sorbitol, glycerol, and low molecular weight polyethylene glycol.

4. The composition according to claim 1, comprising a second film having a dissolution rate in aqueous media that is faster than the dissolution rate in aqueous media of said first film, wherein said second film comprises an active agent selected from an antibacterial agent; a flavor, a fragrance; and a combination of two or more thereof.

5. The composition of claim 1, which is a clear gel toothpaste;
   wherein the pigment is released from said first film after brushing for a period of 30 to 120 seconds.

6. The composition of claim 1, wherein substantially all of the pigment is released from said first film at the same point in time.

7. A method of cleaning the teeth comprising brushing with a composition according claim 1, wherein brushing is continued until the film releases substantially all of the pigment; thereby providing a color signal to the user of adequate brushing.

\* \* \* \* \*